United States Patent [19]

Aurell et al.

[11] Patent Number: 5,459,236
[45] Date of Patent: Oct. 17, 1995

[54] VASOACTIVE VASOTOCIN DERIVATIVES

[75] Inventors: Carl-Johan Aurell; Per Melin, both of Malmö ; Anders Nilsson, Lund; Jerzy Trojnar, Bunkeflostrand, all of Sweden

[73] Assignee: Ferring AB, Malmoe, Sweden

[21] Appl. No.: 923,895

[22] PCT Filed: Feb. 26, 1991

[86] PCT No.: PCT/SE91/00154

§ 371 Date: Sep. 23, 1992

§ 102(e) Date: Sep. 23, 1992

[87] PCT Pub. No.: WO91/13092

PCT Pub. Date: Sep. 5, 1991

[30] Foreign Application Priority Data

Feb. 27, 1990 [SE] Sweden .................................. 9000691

[51] Int. Cl.$^6$ ..................................................... C07K 7/16
[52] U.S. Cl. ........................... 530/315; 530/317; 530/328
[58] Field of Search ...................... 514/11, 15; 530/315, 530/317, 328

[56] References Cited

FOREIGN PATENT DOCUMENTS 0037516  10/1981  European Pat. Off. .
8903393   4/1989  WIPO .

OTHER PUBLICATIONS

Manning et al, The Pituitary, eds. C. Beardwell & G. Robinson, Butterworths, Kent England, pp. 265–296, (1981).
Hruky et al, The Peptides, vol. 8, pp. 77–207, (1987).
Melin et al, CA 108; 198503(f); [European J. Pharmacol. vol. 148(1); pp. 93–99, (1988)].
Br. J. Pharmac., vol. 67, 1979 G. W. Bisset et al.: "Hydroxy Analogues of oxytocin and of lysinevasopressin", see pp. 575–585.
Endocrinology, vol. 112, No. 1, 1983 Dean W. Cheesman et al.: "Anovulatory Effect of Synthetic Analogs of Arginine Vasotocin in the Rat", see pp. 269–276.

Primary Examiner—Jill Warden
Assistant Examiner—T. D. Wessendorf
Attorney, Agent, or Firm—Oblon, Spivak, McClelland, Maier, & Neustadt

[57] ABSTRACT

The present invention relates to new vasotocin derivatives with prolonged activity compared to previous vasotocin derivatives. In particular, the vasotocin derivatives of the present invention are of the formula (I)

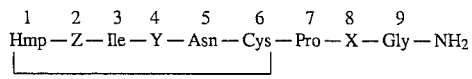

wherein Hmp is a 2-hydroxy-3-mercaptopropionic acid residue,

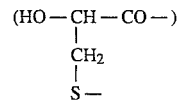

Z is Phe or Tyr, Y is Hgn or Hci, X is a residue of the formula

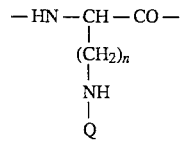

wherein Q is H, alanyl or L-2-aminobutyryl and n is 1, 2 or 3. The present invention also relates to pharmaceutical compositions containing these vasotocin derivatives.

5 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( i x ) FEATURE:
( A ) NAME/KEY: Modified-site
( B ) LOCATION: 1
( D ) OTHER INFORMATION: /note="Phe or Tyr"

( i x ) FEATURE:
( A ) NAME/KEY: Modified-site
( B ) LOCATION: 3
( D ) OTHER INFORMATION: /note="Homoglutamine or homocitrulline"

( i x ) FEATURE:
( A ) NAME/KEY: Disulfide-bond
( B ) LOCATION: 1..5
( D ) OTHER INFORMATION: /note="Position 1 contains an N-linked hydroxymercaptopropionic acid residue, which is S- linked to the 5-Cys."

( i x ) FEATURE:
( A ) NAME/KEY: Modified-site
( B ) LOCATION: 7
( D ) OTHER INFORMATION: /note="Dpr, Dbu or Orn"

( x i ) SEQUENCE DESCRIPTION: SEQ ID NO:1:

Xaa  Ile  Xaa  Asn  Cys  Pro  Xaa  Gly
1                        5

( 2 ) INFORMATION FOR SEQ ID NO:2:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( i x ) FEATURE:
( A ) NAME/KEY: Modified-site
( B ) LOCATION: 3
( D ) OTHER INFORMATION: /note="Homoglutamine"

( i x ) FEATURE:
( A ) NAME/KEY: Disulfide-bond
( B ) LOCATION: 1..5
( D ) OTHER INFORMATION: /note="Position 1 contains an N-linked hydroxymercaptopropionic acid residue, which is S- linked to the 5-Cys."

( i x ) FEATURE:
( A ) NAME/KEY: Modified-site
( B ) LOCATION: 7
( D ) OTHER INFORMATION: /note="Dbu"

( x i ) SEQUENCE DESCRIPTION: SEQ ID NO:2:

Phe  Ile  Xaa  Asn  Cys  Pro  Lys  Gly
1                        5

( 2 ) INFORMATION FOR SEQ ID NO:3:

( i ) SEQUENCE CHARACTERISTICS:
    ( A ) LENGTH: 8 amino acids
    ( B ) TYPE: amino acid
    ( D ) TOPOLOGY: circular ( i i ) MOLECULE TYPE: peptide ( i x ) FEATURE:
    ( A ) NAME/KEY: Modified-site
    ( B ) LOCATION: 3
    ( D ) OTHER INFORMATION: /note="Homocitrulline"

( i x ) FEATURE:
    ( A ) NAME/KEY: Disulfide-bond
    ( B ) LOCATION: 1..5
    ( D ) OTHER INFORMATION: /note="Position 1 contains an
        N-linked hydroxymercaptopropionic acid residue,
        which is S- linked to the 5-Cys."

( i x ) FEATURE:
    ( A ) NAME/KEY: Modified-site
    ( B ) LOCATION: 7
    ( D ) OTHER INFORMATION: /note="Dbu"

( x i ) SEQUENCE DESCRIPTION: SEQ ID NO:3:

Phe  Ile  Xaa  Asn  Cys  Pro  Lys  Gly
1                    5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 3
        ( D ) OTHER INFORMATION: /note="Homoglutamine"

( i x ) FEATURE:
        ( A ) NAME/KEY: Disulfide-bond
        ( B ) LOCATION: 1..5
        ( D ) OTHER INFORMATION: /note="Position 1 contains an
            N-linked hydroxymercaptopropionic acid residue,
            which is S- linked to the 5-Cys."

( i x ) FEATURE:
        ( A ) NAME/KEY: Modified-site
        ( B ) LOCATION: 7
        ( D ) OTHER INFORMATION: /note="Orn"

( x i ) SEQUENCE DESCRIPTION: SEQ ID NO:4:

Tyr  Ile  Xaa  Asn  Cys  Pro  Lys  Gly
1                    5

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 3
        ( D ) OTHER INFORMATION: /note="Homoglutamine"

( i x ) FEATURE:
        ( A ) NAME/KEY: Disulfide-bond (B) LOCATION: 1..5
(D) OTHER INFORMATION: /note="Position 1 contains an
N-linked hydroxymercaptopropionic acid residue,
which is S- linked to the 5-Cys."

(ix) FEATURE:
(A) NAME/KEY: Modified-site
(B) LOCATION: 7
(D) OTHER INFORMATION: /note="Dbu"

(xi) SEQUENCE DESCRIPTION: SEQ ID NO:5:

```
Tyr  Ile  Xaa  Asn  Cys  Pro  Xaa  Gly
 1                   5
```

VASOACTIVE VASOTOCIN DERIVATIVES

The present invention relates to new vasotocin derivatives, more specifically such vasotocin derivatives as differ from the native hormone in that the vasotocin (VT) structure has been modified at positions 1, 4, 8 and optionally 2.

The new VT derivatives are vasoactive, more particularly by specifically raising the blood pressure, and in some cases have a considerably prolonged effect.

BACKGROUND

The peptide hormone vasopressin, produced by the posterior lobe of the pituitary, mainly has two functions, that is the hormone has both an antidiuretic effect (reduced excretion of urine) and a contracting effect on smooth muscles in the vascular wall, the latter effect causing a blood pressure increase and a reduced tendency to bleeding. In clinical use, vasopressin thus has a non-specific effect of short duration.

Today, there is on the market a vasopressin analog having a prolonged effect, namely lysine-vasopressin extended in the N-terminal by three amino acid residues. This vasopressin analog acts as a so-called prohormone or hormonogen, i.e. it increases the duration of the vasopressin effect. The extended vasopressin analog has in itself a very small pharmacological effect which does not occur until the extra N-terminal amino acid residues are cleaved by enzymatic hydrolysis and free lysine-vasopressin is formed. Besides the prolonged effect, such a prohormone is advantageous in that the risk of overdosage is minimized by the limited enzyme capacity of the organism determining the plasma levels of the liberated vasopressin. In this manner, it is possible to avoid excessively high plasma levels of vasopressin possibly leading to abnormally increased blood pressure which may harm the patient. The above-mentioned vasopressin analog however suffers from major drawbacks by having low potency and, like vasopressin, being non-specific.

There is a need for vasoconstrictive substances for use as bleeding inhibitors and in so-called orthostatic hypotension, i.e. conditions of blood pressure drop following changes of body position. These agents should specifically increase blood pressure, thus having a low antidiuretic effect in order to avoid water intoxication in patients subjected to long-term treatment. Also, it is advantageous if they exhibit an effect of long duration.

Recently, we have filed (on Oct. 7, 1987) a Swedish patent application SE 8703855-0 (corresponding to PCT/SE88/00509) comprising vasotocin derivatives having specific blood pressure increasing activity. The vasotocin derivatives according to the present invention differ structurally from the vasotocin derivatives according to said prior Swedish patent application mainly in that they have a further modification at position 4 of the vasotocin structure, i.e. they have homoglutamine or homocitrulline at position 4.

DESCRIPTION OF THE INVENTION

The present new vasoactive vasotocin derivatives specifically increase blood pressure, i.e. they are pressor-specific, meaning a high ratio of blood pressure to antidiuretic activity. In particular the antidiuretic effect (reduced excretion of urine) of the parent molecule is eliminated. Furthermore they have a considerably prolonged effect in some cases. The compounds according to the invention are intended to be used in a pharmaceutical composition for inhibiting bleeding and in conditions of blood pressure drop following changes of body position, so-called orthostatic hypotension, and also as general blood pressure increasing agents. The VT derivatives according to the invention are of the formula (SEQ ID NO: 1).

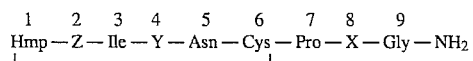

wherein

Hmp=a 2-hydroxy-3-mercaptopropionic acid residue,

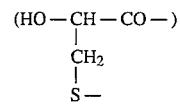

Z=phenylalanine (Phe) or tyrosine (Tyr)
Y=homoglutamine (Hgn) or homocitrulline (Hci)

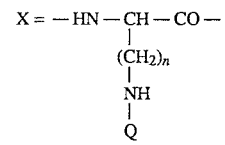

Q=H or from 1 to 3 amino acid residues of the same or different natural or unnatural L– or D-amino acids, and n is 1, 2 or 3.

The VT derivatives according to the invention can be presented in the form of pharmaceutical compositions in which at least one VT derivative according to the invention is included as active ingredient, together with pharmaceutically acceptable additives and/or diluents. The pharmaceutical compositions according to the invention preferably are in the form of preparations suitable for parenteral administration. They are suitably administered by injection, infusion or intranasal application. The diluent may be e.g. a physiological saline solution.

A pharmaceutical composition according to the invention may contain a specifically blood pressure increasing derivative having a relatively short duration for providing an instant effect, in combination with a specifically blood pressure increasing derivative having a long duration for providing a prolongation of the effect.

PREPARATION OF THE VT DERIVATIVES ACCORDING TO THE INVENTION

The VT derivatives according to the invention can be prepared by methods analogous with those which are known in the peptide field.

For instance, the compounds according to the invention can be be prepared in conventional manner by coupling amino acids stepwise to one another in liquid phase, e.g. as disclosed by Law, H. B. & Du Vigneaud, V. in Journal of the American Chemical Society 82, (1960) 4579–4581, Zhuze, A. L., Jŏst, K., Kasafi'rek, E. & Rudinger, J. in Collection of Czechoslovak Chemical Communications 29 (1964), 2648–2662, and modified by Larsson, L.-E., 5 Lindeberg, G., Melin, P. / Pliška, V. in Journal of Medicinal Chemistry21, (1978), 352–356. The coupling of the amino acids to one another, yielding so-called peptide bonds, can also be effected with a solid phase (generally a resin) as starting material to which the C-terminal of the first amino acid is coupled, whereupon the C-terminal of the next amino acid is coupled to the N-terminal of the first amino acid and so on. Finally, the finished peptide is liberated from the solid phase. In the Examples hereinbelow, this so-called solid phase technique has been used in accordance with the disclosure of Merrifield, R. B., J. Am. Chem. Soc. (1963) 85, 2149, Merrifield, R. B. Biochemistry (1964), 3, 1385 and König, W., Geiger, R., Chem. Bar. (1970), 103, 788.

GENERAL DESCRIPTION OF SYNTHESIS

All the VT derivatives prepared in the Examples given below were synthesised on an APPLIED BIOSYSTEMS 430a PEPTIDE SYNTHESIZER using a double coupling program with a termination step after the second coupling. The resin used was of 4-methylbenzhydrylamine type with a theoretical loading of 0.65 meq/g (Peninsula Laboratories Inc., USA). The final product of the synthesis was dried in vacuo overnight. The peptide was then cleaved from the resin by treatment with liquid hydrogen fluoride in the presence of anisole and ethyl-methyl-sulphide as scavengers (HF:anisole:EMS 10:05:05). After removal of hydrogen fluoride by evaporation, the resin was suspended in ethyl acetate (100 ml) and filtered. The solid was washed on filter with additional ethyl acetate (3×100 ml), and the cleaved peptide was extracted with acetic acid (100 ml). The extract was promptly diluted to a volume of 1.5 i with 20% acetic acid in methanol and treated with 0.1M solution of iodine in methanol until a faint brown colour remained. Then a DOWEX 1×8 ion exchanger in acetate form (15 g) (Bio-Rad, Richmond, Calif.) was added and the mixture filtered. The filtrate was evaporated and the residue freeze-dried from water. The product was then purified by reversed phase liquid chromatography on a column filled with KROMASIL® 13μ (EKA Nobel, Surte, Sweden) in a suitable system containing acetonitrile in 0.1% trifluoroacetic acid water solution. The samples collected from the column were analysed by analytical high performance liquid chromatography (HPLC) (Spectra Physics Inc. USA 8800) equipped with a VYDAC 5μ C18 column (Vydac Inc., USA). Fractions containing pure substance were pooled, the solvent was evaporated and the product freeze-dried from water. The final HPLC analysis was performed on ready product, and the structure of the peptide was confirmed by amino acid analysis and fast atom bombardment mass spectrometry (FAB MS).

All amino acids used during the synthesis were L-amino acids, and they were protected with a tert-butoxy-carbonyl group at the α-amino function. The side chains were protected as follows:

Hmp(Mob), Cys(Mob), Dab(Cbz).

The abbreviations within brackets are:

Cbz=carbobenzoxy;

Mob=4-methoxybensyl; and

Boc=t-butyloxycarbonyl

The amino acid derivatives were supplied by Bachem AG, Switzerland.

Further abbreviations used are:

Dab=L-2,4-diaminobutyric acid

Abu=L-2-aminobutyric acid

Hgn=homoglutamine

Hci=homocitrulline

Hmp=2-hydroxy-3-mercaptopropionic acid

OPfp=pentafluorophenyl ester

DIPEA=diisopropylethylamine

EXAMPLE 1

1-Hmp-2-Phe-4-Hgn-8-Dab-VT (SEQ ID NO: 2) [n=2 and Q=H]

The peptide was synthesised according to the general description. 2-hydroxy-mercaptopropionic acid[S-(p-methoxy)benzyl] was used for position 1. Purity (HPLC): 99.5% (18.4% acetonitrile in 0.1% TFA, retention time 9.13 rain at 1.5 ml/min, detection at 223 nm).

The structure was confirmed by amino acid analysis and FAB MS analysis.

EXAMPLE 2

1-Hmp-2-Phe-4-Hgn-8-Dab(Ala)-VT [n=2 and Q=Ala]

The oxidized and purified nonapeptide Hmp-Phe-Ile-Hgn-Asn-Cys-Pro-Dab-Gly-$NH_2$ (SEQ ID NO: 2)(150 mg; prepared by solid phase method according to the general description) was dissolved in DMF (2 ml) and previously formed Boc-Ala-OPfp (4 equivalents) was added and pH was adjusted to 8–8.5 (DIPEA). The reaction mixture was stirred overnight at room temperature. The product was isolated by precipitation with ethyl acetate, filtration and drying in vacuo.

The product was then treated with TFA/$CH_2Cl_2$ 1:1 (20 ml), stirred for 30 min, evaporated and then treated with diethyl ether (100 ml). The precipitation was separated by filtration and dried in vacuo.

The product was purified by reversed phase liquid chromatography.

Purity (HPLC): 99.8% (17.6% acetonitrile in 0.1% TFA, retention time 8.56 min at 2 ml/min, detection at 223 nm).

The structure was confirmed by amino acid analysis and FAB MS analysis.

EXAMPLE 3

1-Hmp-2-Phe-4-Hgn-8-Dab(Abu)-VT [n=2 and Q=Abu]

The oxidized and purified nonapeptide Hmp-Phe-Ile-Hgn-Asn-Cys-Pro-Dab-Gly-$NH_2$ (SEQ ID NO: 2) (100 mg; prepared by solid phase method according to the general description) was dissolved in DMF (2 ml) and previously formed Boc-Abu-OPfp (4 equivalents) was added and pH was adjusted to 8–8.5 (DIPEA). The reaction mixture was stirred overnight at room temperature. The product was isolated by precipitation with ethyl acetate, filtration and drying in vacuo.

The product was then treated with TFA/$CH_2Cl_2$ 1.1 (20 ml ), stirred for 30 min, evaporated and then treated with diethyl ether (100 ml). The precipitation was separated by filtration and dried in vacuo.

The product was purified by reversed phase liquid chromatography.

Purity (HPLC): 99.5% (17.6% acetonitrile in 0.1% TFA, retention time 9.82 min at 2 ml/min, detection at 223 nm).

The structure was confirmed by amino acid analysis and FAB MS analysis.

EXAMPLE 4

1-Hmp-2-Phe-4-Hci-8-Dab-VT (SEQ ID NO: 3) [n=2 and Q=H]

The peptide was synthesised according to the general description. 2-hydroxy-mercaptopropionic acid[S-(p-methoxy)benzyl] was used for position 1. Purity (HPLC): 98.5% (17.6% acetonitrile in 0.1% TFA, retention time 10.68 rain at 2 ml/min, detection at 223 nm).

EXAMPLE 5

1-Hmp-2-Phe-4-Hci-8-Dab(Abu)-VT [n=2 and Q=Abu]

The oxidized and purified nonapeptide Hmp-Phe-Ile-Hci-Asn-Cys-Pro-Dab-Gly-NH$_2$ (SEQ ID NO: 3) (100 mg; prepared by solid phase method according to the general description) was dissolved in DMF (2 ml) and previously formed Boc-Abu-OPfp (4 equivalents) was added and pH was adjusted to 8–8.5 (DIPEA). The reaction mixture was stirred overnight at room temperature. The product was isolated by precipitation with ethyl acetate, filtration and drying in vacuo.

The product was then treated with TFA/CH$_2$Cl$_2$ 1:1 (20 ml), stirred for 30 min, evaporated and then treated with diethyl ether (100 ml). The precipitation was separated by filtration and dried in vacuo.

The product was purified by reversed phase liquid chromatography.

Purity (HPLC): 99.5% (20.0% acetonitrile in 0.1% TFA, retention time 5.94 min at 2 ml/min, detection at 223 nm).

The structure was confirmed by amino acid analysis and FAB MS analysis.

EXAMPLE 6

1-Hmp-4-Hgn-8-Orn-VT [n=2 and Q=H]

The peptide was synthesised according to the general description. 2-hydroxy-mercaptopropionic acid[ 8- (p-methoxy)benzyl] was used for position 1. Purity (HPLC): 98.5% (14.4% acetonitrile in 0.1% TFA, retention time 5.83 min at 2 ml/min, detection at 223 nm).

The structure was confirmed by amino acid analysis and FAB MS analysis.

EXAMPLE 7

1-Hmp-4-Hgn-8-Dab-VT [n=2 and Q=M]

The peptide was synthesised according to the general description. 2-hydroxy-mercaptopropionic acid[ S-(p-methoxy)benzyl] was used for position 1. Purity (HPLC): >99% (18.0% acetonitrile in 0.1% TFA, retention time 4.98 rain at 2 ml/min, detection at 223 nm).

The structure was confirmed by amino acid analysis and FAB MS analysis.

PHARMACOLOGICAL TESTS

Vasotocin derivatives according to the invention have been tested for potency of both blood pressure and antidiuretic activity in a so-called 4-point test, i.e. the activity of the test substances has been related to a standard preparation (AVP=argininevasopressin), and the effects of two dose levels for each substance have been analysed. In addition, three pressor-specific VT derivatives according to our previous application SE 8703855-0 have been tested for a comparison, namely 1-Hmp-2-Phe-S-Orn-VT (compound 2 in Table 1), 1-Hmp-2-Phe-S-Dab-VT (compound 3 in Table 1), and 1-Hmp-2-Phe-S-Dab(Ala)-VT (compound 5 in Table 1).

Blood pressure tests were carried out on anaesthetised Sprague Dawley rats (about 250 g), previously treated with dibenamine (Dekanski, J., 1952. Br. J. Pharmacol. 7, 567). Maximal blood pressure increase after intravenous injections of peptide was used as a measure of the effect, expressed as intensity.

In addition to potency determination based-on effect intensity, a measure of the length of the effect has been stated (index of persistence (I.P.), Pliška, V., 1966. Arzheim. Forech. 16, 886). This dimensionless factor is a measure of the effect duration of the respective analog in relation to the standard AVP.

Antidiuretic potency was determined with the aid of anaesthetised water-loaded Sprague Dawley rats (200 g) (Larsson, L. E., Lindeberg, G., Melin, P. and Pliška, V., 1978, J. Mad. Chem. 21, 353). Maximal increase of urine conductivity after intravenous injections was used as effect parameter.

In these two tests, a comparison was made between the effects of the respective derivative and the effect of a standard preparation, AVP, and potency was determined with the aid of a 4-point test and is indicated in international units per micromole (IU/μmole) (Stürmer, E., in Handbook of Expermimental Pharmacology, 1966, Vol 23, pp 130–189).

The specificity in respect of blood pressure is indicated by the ratio of potency blood pressure/potency antidiuresis (BP/AD).

The pharmacological results are given in Table 1.

From Table 1 it appears that the compounds according to the invention retain a very high potency in respect of blood pressure increase and effect duration.

By the introduction of homoglutamine or homocitrulline at position 4 the antidiuretic activity has been practically eliminated. Thus, the present invention is unique in that the pressor specificity (ratio of blood pressure to antidiuretic activity) has been increased approximately 2 to 10 times in comparison to the already pressor specific derivatives of our SE 8703855-0 (modifications at positions 1, 2 and 8 of the parent molecule; see Table 1).

The combination of this modification with previously made substitutions at positions 1, 2 and 8 has led to analogs with high potency, long duration of action and extreme pressor specificity. Thus, based on the animal experiments presented, the new substances may, in therapy be expected to completely lack any water accumulating effect (antidiuretic), thus totally avoiding the risk of water intoxications of the patients.

EXAMPLE OF THE PREPARATION OF A PHARMACEUTICAL COMPOSITION

The VT derivative is dissolved in distilled water together with mannitol. The solution is poured into an ampoule, subjected to freeze-drying and sealed. The contents in the ampoule can then when desired, be diluted with an isotonic saline solution to a concentration suitable for administration.

TABLE 1

| ANALOG | BLOOD PRESSURE BP | | ANTIDIURESIS AD IU/μmole | BP/AD (measure of specificity) |
|---|---|---|---|---|
| | IU/μmole | I.P (measure of duration of effect) | | |
| 1. AVP (Reference) | 614 ± 25 | 1.0 | 620 ± 54 | 1.0 |
| 2. 1-Hmp-2-Phe-8-Orn-VT | 421 ± 41 | 3.1 ± 1.3 | 9.4 ± 1.1 | 45 |
| 3. 1-Hmp-2-Phe-8-Dab-VT | 657 ± 32 | 2.7 ± 0.6 | 18 ± 2.1 | 37 |
| 4. 1-Hmp-2-Phe-4-Hgn-8-Dab-VT (Ex. 1(SEQIDNO:2)) | 214 ± 6 | 2.3 ± 0.5 | 0.3 ± 0.02 | 713 |
| 5. 1-Hmp-2-Phe-8-Dab(Ala)-VT | 360 ± 31 | 6.7 ± 1.5 | 4.3 ± 0.3 | 84 |
| 6. 1-Hmp-2-Phe-4-Hgn-8-Dab(Ala)-VT (Ex. 2) | 117 ± 6 | 6.6 ± 1.0 | 0.2 ± 0.02 | 585 |
| 7. 1-Hmp-2-Phe-4-Hgn-8-Dab(Abu)-VT (Ex. 3) | 163 ± 15 | 8.6 ± 2.3 | 0.2 ± 0.01 | 858 |
| 8. 1-Hmp-2-Phe-Hci-8-Dab-VT (Ex. 4SEGIDNO:3) | 157 ± 13 | 1.7 ± 0.05 | 0.3 ± 0.05 | 523 |
| 9. 1-Hmp-2-Phe-4-Hci-8-Dab(Abu)-VT (Ex. 5) | 67 ± 5 | 3.6 ± 0.7 | 0.2 ± 0.04 | 335 |
| 10. 1-Hmp-4-Hgn-8-Orn-VT (Ex. 6) Seq.ID.No. 4 | 473 ± 62 | 7.3 ± 1.8 | 1.0 ± 0.2 | 473 |
| 11. 1-Hmp-4-Hgn-8-Dab-VT (Ex. 7) | 536 ± 53 | 3.8 ± 0.8 | 2.9 ± 0.5 | 185 |

We claim:

1. A vasotocin derivative of the formula

```
 1    2   3    4    5    6    7   8    9        SEQ. ID. NO 2
Hmp — Z — Ile — Y — Asn — Cys — Pro — X — Gly — NH₂
 |_____|
``` wherein Hmp is a 2-hydroxy-3-mercaptopropionic acid residue of the formula $$\begin{array}{c} (HO-CH-CO-) \\ | \\ CH_2 \\ | \\ S- \end{array}$$

Z is Phe,
Y is Hgn, and
X is

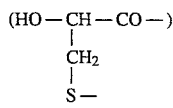

wherein Q is H and n is 2.

2. A vasotocin derivative of the formula

```
 1    2   3    4    5    6    7   8    9
Hmp — Z — Ile — Y — Asn — Cys — Pro — X — Gly — NH₂
 |_____|
``` wherein Hmp is a 2-hydroxy-3-mercaptopropionic acid residue of the formula $$\begin{array}{c} (HO-CH-CO-) \\ | \\ CH_2 \\ | \\ S- \end{array}$$

Z is Phe,
Y is Hgn, and
X is

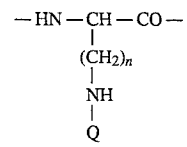

wherein n is 2 and Q is alanyl.

3. A vasotocin derivative of the formula

```
 1    2   3    4    5    6    7   8    9
Hmp — Z — Ile — Y — Asn — Cys — Pro — X — Gly — NH₂
 |_____|
``` wherein Hmp is a 2-hydroxy-3-mercaptopropionic acid residue of the formula $$\begin{array}{c} (HO-CH-CO-) \\ | \\ CH_2 \\ | \\ S- \end{array}$$

Z is Phe,
Y is Hgn, and
X is

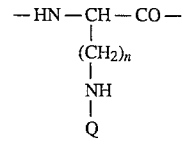

wherein n is 2 and Q is L-2-aminobutyryl.

4. A vasotocin derivative of the formula

```
 1    2   3    4    5    6    7   8    9        SEQ. ID. NO 3
Hmp — Z — Ile — Y — Asn — Cys — Pro — X — Gly — NH₂
 |_____|
``` wherein Hmp is a 2-hydroxy-3-mercaptopropionic acid residue of the formula

Z=Phe,
Y=Hci, and
X is
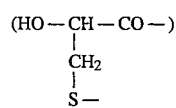
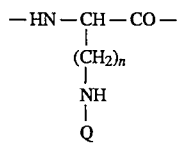
wherein n is 2 and Q is H.
5. A vasotocin derivative of the formula
```
  1    2    3    4    5    6    7   8    9    SEQ. ID. NO 4
Hmp — Z — Ile — Y — Asn — Cys — Pro — X — Gly — NH2
              |_____|
```
wherein Hmp is a 2-hydroxy-3-mercaptopropionic acid residue of the formula
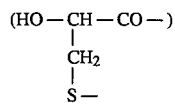
Z is Tyr,
Y is Hgn, and
X is
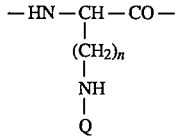
wherein n is 3 and Q is H.
* * * * *